(12) United States Patent
Tyagi et al.

(10) Patent No.: US 7,728,136 B2
(45) Date of Patent: Jun. 1, 2010

(54) METHOD FOR THE PREPARATION OF ARYL PIPERAZINYL-HETEROCYCLIC COMPOUNDS

(75) Inventors: Om Dutt Tyagi, Pune (IN); Tushar Kumar Srivastava, Pune (IN); Yogendra Kumar Chauhan, Pune (IN); Vasanth Kumar Nalam, Pune (IN)

(73) Assignee: Lupin Limited, Mumbai (IN)

( * ) Notice: Subject to any disclaimer, the term of this patent is extended or adjusted under 35 U.S.C. 154(b) by 743 days.

(21) Appl. No.: 11/630,054

(22) PCT Filed: Jun. 16, 2005

(86) PCT No.: PCT/IN2005/000205

§ 371 (c)(1),
(2), (4) Date: Dec. 18, 2006

(87) PCT Pub. No.: WO2006/011157

PCT Pub. Date: Feb. 2, 2006

(65) Prior Publication Data

US 2007/0238877 A1    Oct. 11, 2007

(30) Foreign Application Priority Data

Jun. 18, 2004    (IN)    ................ 662/MUM/2004

(51) Int. Cl.
*C07D 419/06*    (2006.01)
(52) U.S. Cl. ..................................... 544/368
(58) Field of Classification Search .................. 544/368
See application file for complete search history.

(56) References Cited

U.S. PATENT DOCUMENTS

| 4,831,031 A | 5/1989 | Lowe, III et al. |
| 5,206,366 A | 4/1993 | Bowles |
| 5,338,846 A | 8/1994 | Busch et al. |

FOREIGN PATENT DOCUMENTS

| EP | 0 281 309 A1 | 9/1988 |
| EP | 0 584 903 A1 | 3/1994 |
| WO | 2005/040160 A2 | 5/2005 |
| WO | 2005/040160 A3 | 5/2005 |

OTHER PUBLICATIONS

Valenta et al. "Potential Nootropic Agents: Synthesis of a Series of (2-Oxo-1-Pyrrolidinyl)Acetic Acid Piperazides" Collect. Czech. Chem. Commun. (vol. 55) (1990). p. 1613-1629.

*Primary Examiner*—James O Wilson
*Assistant Examiner*—Ebenezer Sackey
(74) *Attorney, Agent, or Firm*—Merchant & Gould P.C.

(57) ABSTRACT

A novel method for preparing a compound of formula I

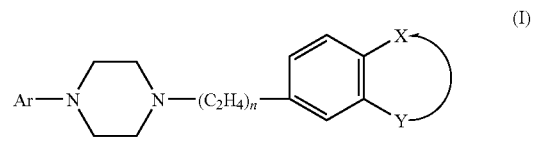

which comprises of coupling the piperazine derivative of formula II

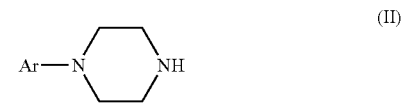

with alkyl halide containing compound of the formula III

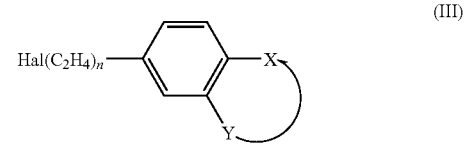

by heating in solvent free conditions or, optionally, in a minimum quantity of non-aqueous suspending liquid, in presence of a catalyst and a neutralizing agent to neutralize the hydrohalic acid.

11 Claims, No Drawings

METHOD FOR THE PREPARATION OF ARYL PIPERAZINYL-HETEROCYCLIC COMPOUNDS

FIELD OF INVENTION

The present invention relates to a novel method for the preparation of arylpiperazinyl-ethyl (or butyl)-heterocyclic compounds of formula (I) by reacting N-arylpiperazine compound of formula (II) with a alkyl halide compound of the formula (III) without any solvent or optionally with minimum amount of non aqueous suspending liquid. In particular, the present invention relates to a process for the manufacture of Ziprasidone, chemically known as 5-(2-(4-(1,2-benzisothiazol-3-yl)-1-piperazinyl)ethyl)-6-chloro-1,3-dihydro-2H-indol-2-one, which is an antipsychotic agent used for the treatment of schizophrenia.

BACKGROUND OF THE INVENTION

U.S. Pat. No. 4,831,031 discloses that arylpiperazinyl-ethyl (or butyl)-heterocyclic compounds of formula (I) may be prepared by reacting piperazines of the formula (II) with compounds of the formula (III) in a polar organic solvent; in the presence of a tertiary amine base or alkali metal base, and in the further presence of catalytic amount of sodium iodide. The final product is purified by chromatography.

Ziprasidone covered in '031 is synthesized by the coupling reaction of 3-piperazinylbenzo[d]isothiazole and 6-chloro-5-(2-chloroethyl)indolin-2-one.

The abovementioned method suffers from the following disadvantages,

1) Longer reaction time of 24 to 72 hours,
2) Formation of considerable quantities of by products,
3) Environmental burden of handling and disposal of aqueous and non aqueous effluents,
4) Special purification techniques like chromatography and,
5) Variable yields ranging from 14 to 84%.

U.S. Pat. No. 5,206,366 discloses a process for making (I), in particular Ziprasidone, by reacting equimolar amounts of (II) and (III) in water and in the presence of a neutralizing agent such as $Na_2CO_3$, at refluxing temperature for about 9 to 12 hours.

Further U.S. Pat. No. 5,338,846 discloses a process for the preparation of hydrochloride salt of (I), in particular Ziprasidone, by refluxing an equimolar mixture of hydrochloride salt of (II) with (III) in water and in presence of a neutralizing agent $Na_2CO_3$ for about 8 to 16 hours.

The methods disclosed in '366 and '846 uses large excess of neutralizing agent and water resulting in voluminous reaction mixture and chances of residual carbonate impurities in the final product.

Surprisingly, we have found that the above coupling reaction to manufacture (I) could be achieved by mixing (II) and (III) and heating to an appropriate temperature without the use of any solvent or optionally as a suspension in a minimum quantity of a non-aqueous suspending liquid in the presence of a neutralizing agent and catalytic amount of alkali metal halide. The reaction occurs in the fused state by the melting of one of the reactants and the resulting suspension will facilitate proper mixing and better heat transfer.

The process of present invention thus dispenses with the need for using large amounts of solvents for the coupling process as in the prior-art methods.

SUMMARY OF THE INVENTION

Thus according to the main aspect of the present invention there is provided a novel method for the preparation of compounds of formula I

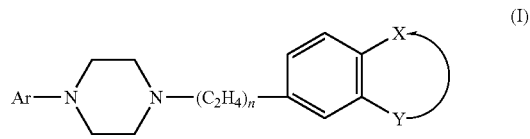

wherein Ar is naphthyl optionally substituted with one to four substituents independently selected from fluoro, chloro, trifluoromethyl, methoxy, cyano and nitro; quinolyl; isoquinolyl; quinazolyl; 6-hydroxy-8-quinolyl; benzoisothiazolyl or an oxide or dioxide thereof, each optionally substituted with one or more substituents independently selected from fluoro, chloro, trifluoromethyl, methoxy, cyano, and nitro; benzothiazolyl; benzothiadiazolyl; benzotriazolyl; benzoxazolyl; benzoxozolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached, form a ring system selected from quinolyl; 2-hydroxyquinolyl; benzothiazolyl; 2-aminobenzothiazolyl; benzoisothiazolyl; indazolyl; 3-hydroxyindazolyl; indolyl; spiro[cyclopentane-1,3'-indolinyl]; and oxindolyl; wherein said ring system may optionally be substituted with one to three substituents independently selected from (C1-C3) alkyl, or with one substituent selected from chloro, fluoro; benzoxazolyl; 2-aminobenzoxazolyl; benzoxozolonyl; 2-aminobenzoxazolinyl; benzothiazolonyl; benzoimidazolonyl; or benzotriazolyl; and phenyl optionally substituted with one chloror or fluoro; said process comprises reacting a monosubstituted piperazine of the formula II

wherein Ar is as defined above, with an alkyl halide containing compound of the formula III

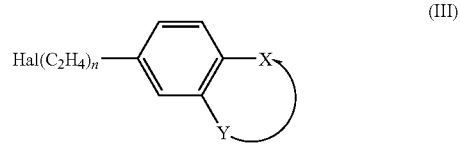

wherein n, X and Y are as defined above and Hal is fluoro, chloro, bromo or iodo, by heating in solvent free conditions or optionally as a suspension in minimum quantity of non-aqueous suspending liquid, in presence of a catalyst and a neutralizing agent.

DETAILED DESCRIPTION OF THE INVENTION

In the process of the present invention the coupling is effected by heating the mixture of (II) and (III) at a temperature in the range of 50° C. to 150° C., preferably between 70° C. to 120° C. and more preferably between 90° C. to 100° C. in the presence of a neutralizing base, such as organic base as well as alkali metal carbonate, for instance potassium carbonate and catalytic amount of alkali metal halide such as, potassium iodide without any solvent or optionally as a suspension in a minimum quantity of a non-aqueous suspending liquid, for example, sulfolane or diphenyl oxide or paraffin. The reaction occurs in the fused state by the melting of one of the reactant and the suspension will facilitate proper mixing and better heat transfer.

Preferred compound manufactured using the process of the present invention is 5-(2-(4-(1,2-benzisothiazol-3-yl)-1-piperazinyl)ethyl)-6-chloro-1,3-dihydro-2H-indol-2-one.

The process has the following advantages over prior-art processes,
(1) Does not require tedious purification procedures such as chromatographic separation.
(2) As no solvent or optionally a minimum of suspending liquid is used, the problems associated with handling and disposal of aqueous and non-aqueous effluents and also those of residual solvent in the finished product are dispensed with.
(3) Smaller reaction volume facilitates scaling up of the reaction.

The invention is further illustrated by the following non-limiting examples.

Example 1

Preparation of 5-(2-(4-(1,2-benzisothiazol-3-yl)-1-piperazinyl)ethyl)-6-chloro-1,3-dihydro-2H-indol-2-one (Ziprasidone)

In a 50 ml 3 necked round bottom flask there were placed 1 gram (4.56 mmol) of 3-piperazinylbenzo[d]isothiazole; 1.25 grams (5.43 mmol) of 6-chloro-5-(2-chloroethyl)indolin-2-one; 50 mg of potassium iodide; 0.82 gram (5.94 mmol) of potassium carbonate and 3 ml of sulfolane. The contents of the flask were heated to 95° C. to 100° C. The reaction was monitored by HPLC. After completion of the reaction, 50 ml of DM water was added to the reaction mixture and stirred. The product was filtered off and washed with water and dried to obtain 1.41 grams (75%) of 5-(2-(4-(1,2-benzisothiazol-3-yl)-1-piperazinyl)ethyl)-6-chloro-1,3-dihydro-2H-indol-2-one. The crude product was purified by IPA and/or THF. The product matched the spectra of a standard NMR and showed the correct retention time by HPLC with 98.0% assay. The melting point of the compound was found to be 218° C.-220° C., and was found to conform with the melting point of 218°-220° C. as disclosed in U.S. Pat. No. 5,206,366.

Example 2

Preparation of 5-(2-(4-(1,2-benzisothiazol-3-yl)-1-piperazinyl)ethyl)-6-chloro-1,3-dihydro-2H-indol-2-one (Ziprasidone)

In a 50 ml 3 necked round bottom flask there were placed 1 gram (4.56 mmol) of 3-piperazinylbenzo[d]isothiazole; 2.5 grams (10.86 mmol) of 6-chloro-5-(2-chloroethyl)indolin-2-one; 50 mg of potassium iodide; 1.64 grams (11.88 mmol) of potassium carbonate. The contents of the flask were heated to 90° C. The reaction was monitored by HPLC. After completion of the reaction, 50 ml of DM water was added to the reaction mixture and stirred. The product was filtered off and washed with water and dried to obtain 1.41 grams (75%) of 5-(2-(4-(1,2-benzisothiazol-3-yl)-1-piperazinyl)ethyl)-6-chloro-1,3-dihydro-2H-indol-2-one. The crude product was purified by IPA and/or THF. The product matched the spectra of a standard NMR and showed the correct retention time by HPLC with 98.0% assay. The melting point of the compound was found to be 218° C.-220° C., and was found to conform with the melting point of 218° C.-220° C. as disclosed in U.S. Pat. No. 5,206,366.

Example 3

Preparation of 5-(2-(4-(1,2-benzisothiazol-3-yl)-1-piperazinyl)ethyl)-6-chloro-1,3-dihydro-2H-indol-2-one (Ziprasidone)

In glass-lined reactor placed 21.1 Kg (96.34 mole) of 3-piperazinylbenzo[d]isothiazole; 31 kg (134.7 moles) of 6-chloro-5-(2-chloroethyl)indolin-2-one; 1.1 kg of potassium iodide; 20.0 kg (111.92 mole) of potassium carbonate and 63.2 lit of sulfolane. The contents of the flask were initially heated to 75° C. to 80° C. for 2 hrs. Then temperature was raised to 95° C. to 100° C. and stirred till completion of the reaction. After completion of the reaction 210 lit of DM water was added to the reaction mixture and stirred. The product was filtered off and washed with water and dried to obtain 29.75 kg of 5-(2-(4-(1,2-benzisothiazol-3-yl)-1-piperazinyl)ethyl)-6-chloro-1,3-dihydro-2H-indol-2-one (Ziprasidone).

Example 4

Purification of 5-(2-(4-(1,2-benzisothiazol-3-yl)-1-piperazinyl)ethyl)-6-chloro-1,3-dihydro-2H-indol-2-one (Ziprasidone)

Crude Ziprasidone was suspended in 10% IPA in water and stirred for 30 min, solid obtained was filtered and washes with water and acetone and then solid was dried under vacuum to obtained 5-(2-(4-(1,2-benzisothiazol-3-yl)-1-piperazinyl)ethyl)-6-chloro-1,3-dihydro-2H-indol-2-one (Ziprasidone)

Example 5

Purification of 5-(2-(4-(1,2-benzisothiazol-3-yl)-1-piperazinyl)ethyl)-6-chloro-1,3-dihydro-2H-indol-2-one (Ziprasidone)

In glass-lined reactor placed 16 kg of crude 5-(2-(4-(1,2-benzisothiazol-3-yl)-1-piperazinyl)ethyl)-6-chloro-1,3-dihydro-2H-indol-2-one, dissolved in 1120 lit of THF at 65-66° C. The clear solution was treated with 2.4 kg of activated carbon at 64-66° C. for 15 min and filtered while hot. The filtrate was concentrated up to 10 volume and mixed with equal amount of methanol. The solid thus obtained was filtered to get 5-(2-(4-(1,2-benzisothiazol-3-yl)-1-piperazinyl)ethyl)-6-chloro-1,3-dihydro-2H-indol-2-one (Ziprasidone)

The invention claimed is:

1. A process for preparing a compound of formula (I):

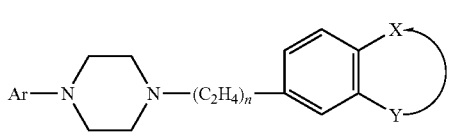

wherein
Ar is naphthyl optionally substituted with one to four substituents independently selected from fluoro, chloro, trifluoromethyl, methoxy, cyano and nitro; quinolyl; isoquinolyl; quinazolyl; 6-hydroxy-8-quinolyl; benzoisothiazolyl or an oxide or dioxide thereof, each optionally substituted with one or more substituents independently selected from fluoro, chloro, trifluoromethyl, methoxy, cyano, and nitro; benzothiazolyl; benzothiadiazolyl; benzotriazolyl; benzoxazolyl; benzoxozolonyl; indolyl; indanyl optionally substituted by one or two fluoro; 3-indazolyl optionally substituted by 1-trifluoromethylphenyl; or phthalazinyl;

n is 1 or 2; and

X and Y together with the phenyl to which they are attached, form a ring system selected from quinolyl; 2-hydroxyquinolyl; benzothiazolyl; 2-aminobenzothiazolyl; benzoisothiazolyl; indazolyl; 3-hydroxyindazolyl; indolyl; spiro[cyclopentane-1,3'-indolinyl]; and oxindolyl; wherein the ring system may optionally be substituted with one to three substituents independently selected from (C1-C3) alkyl, or with one substituent selected from chloro, fluoro; benzoxazolyl; 2-aminobenzoxazolyl; benzoxozolonyl; 2-aminobenzoxazolinyl; benzothiazolonyl; benzoimidazolonyl; or benzotriazolyl; and phenyl optionally substituted with one chloror or fluoro;

the process comprises reacting a monosubstituted piperazine of the formula II

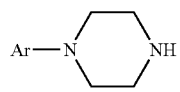

wherein Ar is as defined above, with an alkyl halide containing compound of the formula III

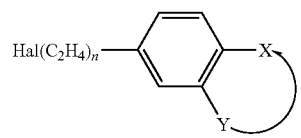

wherein n, X and Y are as defined above and Hal is fluoro, chloro, bromo or iodo, by heating in solvent free conditions or, optionally, as suspension in minimum quantity of non-aqueous suspending liquid, in presence of an alkali metal halide catalyst and a neutralizing agent.

2. A process according to claim 1 wherein the compound of the formula I is 5-(2-(4-(1,2-benzisothiazol-3-yl)-1-piperazinyl)ethyl)-6-chloro-1,3-dihydro-2H-indol-2-one.

3. A process according to claim 1 wherein the compounds of formula II and formula III are reacted under solvent free conditions.

4. A process according to claim 1 wherein the compounds of formula II and formula III are reacted in a suspending liquid.

5. A process according to claim 1 wherein the suspending liquid is selected from sulfolane, diphenyl oxide, paraffin.

6. A process according to claim 1 wherein the temperature is between 50 to 150° C.

7. A process according to claim 1 wherein the temperature is 90° to 100° C.

8. A process according to claim 1 wherein from about one to five molar equivalents of a neutralizing base based on the substrate is used.

9. A process according to claim 1 wherein the catalyst is an alkali metal iodide.

10. A process according to claim 6, wherein the temperature is 70° C. to 120° C.

11. A process according to claim 1, wherein the catalyst is potassium iodide or sodium iodide.

* * * * *